United States Patent [19]

Edwards

[11] Patent Number: 4,918,201

[45] Date of Patent: Apr. 17, 1990

[54] PROCESS FOR PREPARATION OF MALEIC ANHYDRIDE

[75] Inventor: Robert C. Edwards, Naperville, Ill.

[73] Assignee: Amoco Corporation, Chicago, Ill.

[21] Appl. No.: 328,575

[22] Filed: Mar. 27, 1989

Related U.S. Application Data

[62] Division of Ser. No. 150,223, Jan. 29, 1988, Pat. No. 4,861,738.

[51] Int. Cl.$^4$ ............................................. C07D 307/60
[52] U.S. Cl. .................................... 549/259; 549/260
[58] Field of Search .............................. 549/259, 260

[56] References Cited

U.S. PATENT DOCUMENTS 4,020,174 4/1977 Partenheimer ..................... 549/259
4,089,807 5/1978 Partenheimer ..................... 502/35
4,094,816 6/1978 Partenheimer ..................... 502/35
4,780,548 10/1988 Edwards et al. ................... 549/260

*Primary Examiner*—Mary C. Lee
*Assistant Examiner*—Bernard I. Dentz
*Attorney, Agent, or Firm*—Gunar J. Blumberg; William H. Magidson; Ralph C. Medhurst

[57] ABSTRACT

The present invention relates to a process for the regeneration and stabilization of certain phosphorus-vanadium-oxygen complex catalysts or phosphorus-vanadium-oxygen co-metal complex catalysts, with halogen-containing components and subsequently treating the catalyst with phosphorus compounds. These catalysts are useful for the manufacture of maleic anhydride from butane feedstock.

10 Claims, No Drawings

PROCESS FOR PREPARATION OF MALEIC ANHYDRIDE

This is a division of application Ser. No. 150,223, filed Jan. 29, 1988 now U.S. Pat. No. 4,861,738.

BACKGROUND

FIELD OF THE INVENTION

The field of art to which this invention pertains is to regeneration and stabilization of phosphorus-vanadium-oxygen complex catalysts and, in particular, the stabilization of catalysts used for the production of oxygenated products including aldehydes, ketones, acids, anhydrides, and mixtures thereof from hydrocarbon feedstocks. In a specified instance, the claimed regeneration and stabilization procedure is advantageously used on a catalyst used for the production of maleic anhydride from a specified feedstock, namely, normal butane in air. Pertinent U.S. Patent and Trademark Office classifications include Class 549, subclass 259.

BACKGROUND OF THE INVENTION

In general, catalysts proposed for the oxidation of butane, other $C_4$ hydrocarbons, and benzene to maleic anhydride have been based upon vanadium and phosphorus. In U.S. Pat. No. 3,293,268, it is disclosed that the oxidation of butane to maleic anhydride can be performed in the presence of a phosphorus-vanadium-oxygen-containing complex catalyst. Though this catalyst is capable of oxidizing butane, it does not give sufficiently high yields of maleic anhydride. Yields of maleic anhydride of only 30 to 50 weight percent are reported. Various activators, stabilizers, and promoters have been disclosed in the prior art to improve the yields of maleic anhydride. References include U.S. Pat. Nos. 3,867,411; 3,832,359; 3,888,886; 4,002,650; 4,147,661; 4,149,992; 4,151,116; 4,152,338; 4,152,339; 4,081,460; 4,043,943; 4,154,703; and British Application 2,019,839A. While the aforementioned prior art tends to bring about some improvement in the performance of the phosphorus-vanadium catalyst, there remains much room for improvement, particularly from the standpoint of high conversion, yield, and catalyst life. U.S. Pat. No. 4,081,460 relates to molybdenum-vanadium catalysts which are regenerated by the addition of phosphorus. Other references of interest include U.S. Pat. Nos. 4,002,174; 4,094,816; 4,089,807; 3,296,282; 3,474,041; and British Patent 1,464,198.

SUMMARY OF THE INVENTION

Our invention is a process for the in situ regeneration and stabilization of aged hydrocarbon oxidation catalysts whose selectivity to maleic anhydride has declined. The aged catalyst is first treated with a carbon halide compound which removes the old surface of the catalyst. A phosphorus compound is then added to the catalyst feed stream to generate the optimum P/V atomic ratio at the active catalyst sites. A surprising feature of this invention is the combined use of two entirely different regeneration processes to produce a catalyst having a performance which is superior to that produced by either of the processes alone.

The selectivity of butane oxidation catalysts which comprise primarily phosphorus and vanadium declines with time depending on feed rates and operating temperatures. This decline in selectivity generally is caused by the loss of phosphorus from the catalyst surface leading to active sites which do not have an optimum P/V atomic ratio. This loss in selectivity leads to a higher feedstock variable cost, reduced production of maleic anhydride, and poorer product quality. To replace this catalyst is very expensive in terms of the lost production while the unit is shut down, the labor required to change the catalyst, and most importantly, the cost of the new catalyst which is very expensive.

If this catalyst can be regenerated and stabilized, the economic savings are substantial. We disclose herein a novel process which regenerates and stabilizes a butane oxidation catalyst which has declined in selectivity. Moreover, this process requires no unit modifications and minimal unit downtime. The yield of maleic anhydride obtained from a catalyst regenerated by our novel process is higher than the yield obtained from the singular use of either the carbon halide regeneration or regeneration with phosphorus compounds.

In our novel catalyst regeneration process, the catalyst which has declined in yield is first treated in situ with carbon halides such as $CCl_4$ to remove the catalyst surface. This is suitably carried out by adding the carbon halide to the feed stream of n-butane and air during the production of maleic anhydride or to a carrier gas such as nitrogen when the oxidation is discontinued. It is preferred to add the carbon halide to nitrogen carrier gas which is passed over the catalyst bed. The temperature of the catalyst during the carbon halide treatment should be 300° C. to 550° C. Temperatures between 350° C. and 500° C. are preferred. The amount of carbon halide such as carbon tetrachloride added to the catalyst is suitably varied from about 0.005 g $CCl_4$/g catalyst to about 0.5 g $CCl_4$/g catalyst depending upon the amount of catalyst surface removal desired. The preferred range for most catalysts is 0.01–0.1 g $CCl_4$/g catalyst. The flow rate of carrier gas such as nitrogen or butane-air feed is also suitably varied from 100 to 3000 VHSV depending on the concentration of carbon halide or $CCl_4$ desired in the carrier gas or feed. A nitrogen flow rate of 100–1000 VHSV is preferred to minimize nitrogen usage and to maintain a sufficient concentration of carbon halide in the nitrogen stream. The concentration of carbon halide feed or carrier gas stream are also a function of the carbon halide addition rate. Addition times suitably range from 1–60 minutes but times of 10–30 minutes are preferred. Practical concentrations of carbon halide in the feed or carrier gas are suitably about 1 to about 80 mole percent. Preferred concentrations of carbon halide are about 5 to about 50 mole percent and are dependent on the flow rate of the feed or carrier gas and addition time of the carbon halide to that stream.

Once the catalyst has been treated with carbon halide such as $CCl_4$ and the catalyst has reactivated, phosphorus compounds such as triethylphosphate are added continuously to the butane-air feed stream to optimize the P/V ratio on the surface of the catalyst and increase the yield of maleic anhydride from the catalyst. Other alkylphosphates such as trimethylphosphate, phosphites such as trimethylphosphite and triethylphosphite, and phosphines are examples of phosphorus compounds that are usually added to the feed stream in place of triethylphosphate. These compounds are added with or without water, but the presence of a small amount of water in the feed is preferred. The water present in the air feed to the reactor may be sufficient for good performance. The amount of water added is about 1,000 parts per million to about 40,000 parts per million by weight of the reactor feedgas stream. Feedstocks such as butadiene and butenes may also be used in this invention to produce maleic anhydride.

DETAILED DESCRIPTION OF THE INVENTION

A broad embodiment of this invention resides in a method for regenerating and stabilizing a phosphorus-vanadium-oxygen complex catalyst having an atomic ratio of phosphorus to vanadium in the range of from about 0.5 to about 5, which method comprises contacting the catalyst with an effective amount of a reactivating material selected from the group consisting of: (1) molecular chlorine or fluorine, or mixtures thereof; (2) halides of fluorine, chlorine, bromine, or iodine, being in the vapor state above 250° C. at atmospheric pressure, represented by the following formula $C(X)_n$, where each X is a selected halide and n is an integer from about 1 to 4, any remaining radicals being hydrogen or mixtures thereof; (3) organic halides of fluorine, chlorine, bromine or iodine being in the vapor state above about 250° C. at atmospheric pressure represented by the formula $R(X_1)_m$, where R is alkane, alkene or alkyne, of straight or branched structure, having at least two carbon atoms and $X_1$ is independently a primary, secondary, or tertiary halide and m is an integer of from 1 to about 20 consistent with the number of carbon atoms of said structure, or mixtures thereof; (4) hydrogen halides or mixtures thereof at reactivating conditions including a temperature in the range of from about 300° C. to about 550° C.

The catalyst is then further regenerated and stabilized by the addition of phosphorus compounds or mixtures thereof such as alkylphosphates, phosphites, and phosphines. This further regeneration and stabilization takes place at a temperature of about 300° C. to about 550° C. Representative phosphorus compounds have the following structure:

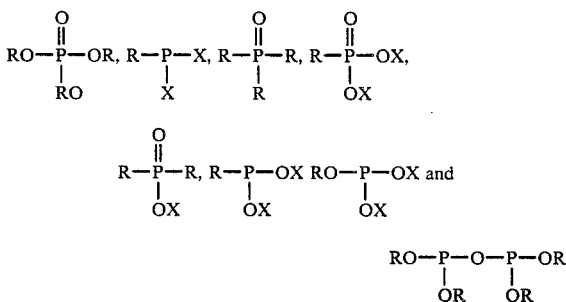

wherein R is a phenyl or an alkyl radical of 1 to 6 carbon atoms and X is H or R. Suitable compounds are primary, $RPH_2$, secondary, $R_2PH$, and tertiary, $R_3P$, phosphines; such as ethyl phosphine; the tertiary phosphine oxides, $R_3PO$, such as tripropyl phosphine oxide; the primary $RP(O)(OX)_2$, and secondary, $R_2P(O)OX$, phosphonic acids, such as benzene phosphonic acid; the esters of the phosphonic acids, such as diethyl methanephosphonate; the phosphonous acids, $RPO_2X_2$, such as benzenephosphonous acid and the esters thereof, such as the monoethyl ester; the phosphinous acids, $R_2POX$, such as diethyl phosphinous acid and the esters thereof, such as the monoethyl ester; the primary, $ROP(OX)_2$, secondary, $(RO)_2POX$, and tertiary, $(RO)_3P$, phosphites, such as diethyl phosphite, trimethyl phosphite, triethyl phosphite, triisopropyl phosphite, tripropyl phosphite and tributyl phosphite, and the pyrophosphites, such as tetraethyl pyrophosphite. The preferred phosphorus compound is an ester of orthophosphoric acid having the formula $(RO)_3P=O$ wherein R is hydrogen or $C_1$-$C_4$ alkyl, at least one R being $C_1$-$C_4$ alkyl. The preferred phosphorus compounds are triethylphosphate or trimethylphosphate.

In another embodiment of this invention, the phosphorus-vanadium-oxygen complex catalyst may include a cometal. Suitable cometals include molybdenum, zinc, tungsten, uranium, titanium, zirconium, antimony, niobium, cobalt, chromium, tin, iron, manganese, nickel, or mixtures thereof.

The present regeneration and stabilization process is useable for many phosphorus-vanadium-oxygen complex catalysts. In fact, these catalysts contain phosphorus, vanadium, and oxygen, and advantageously they include other metals for activation or stabilization of the catalyst.

A representative list of catalysts which can be utilized to produce maleic anhydride from butane or aromatic materials or mixtures thereof are described in the following U.S. Pat. Nos., 3,867,411; 3,832,359; 3,888,886; 4,002,650; 4,147,661; 4,149,992; 4,151,116; 4,152,338; 4,152,339; 4,081,460; 4,043,943; 4,154,703.

The specific oxygenated product will depend on reaction conditions, feedstock selection and catalyst type utilized. Hydrocarbon feedstocks and the products produced therefrom include: ethane and products which are produced from it generally of non-acidic materials; propane which can produce acrylic acid, acetic acid, maleic acid, and, in some instances, propionic acid; normal butane, butenes or butadienes which can produce in certain instances, maleic anhydride and other products including acetic acid, acrylic acid, and methyl acrylic acids; normal pentane, which can produce maleic anhydride and other materials including formic acid and other trace materials; propylene, which can be used to produce maleic anhydride and other acid products, paraxylene, which can be used to produce maleic anhydride; orthoxylene, which can be used to produce phthalic anhydride and, in some cases, maleic anhydride; benzene, which can produce, in many instances, high concentrations of maleic anhydride and other acetic-based materials.

The catalysts contemplated for use in the claimed regeneration and stabilization process are generally made from the reaction of vanadium pentoxide and phosphoric acid under controlled conditions. Other vanadium and phosphorus-containing materials can be used in the catalyst preparation. Various cometals may be added to the phosphorus-vanadium oxide catalyst to improve activity or selectivity. Depending on the feed to be processed and the desired products, the composition of the catalyst can be varied significantly.

For maleic anhydride production from normal butane, a suitable catalyst has an atomic ratio of phosphorus to vanadium of from about 0.5 to about 5. An even more preferred ratio is a value of from around 1.0 to about 1.6. Other metals may be incorporated into the basic catalyst in varying ratios of from about 0.001 to about 5 atoms of activator for each atom of vanadium. An especially useful catalyst for maleic anhydride production from normal butane has an atomic ratio of phosphorus to vanadium to zinc of about 1.15:1.0:0.19.

The concentration of the regenerating agent passing over the catalyst should be monitored so as to prevent damage to the catalyst from excess additions. Additional problems associated with regeneration agent additions include the production of corrosive end products which possibly could damage plant equipment.

It has been found in determining what is an effective amount of regeneration agent that there is some minimum concentration of the regeneration agent which should be passed into the reaction zone to effect the increase in selectivity of the catalyst. However, it is difficult to ascertain the concentration as an absolute quantity since reactor designs would have a substantial influence on the actual concentration to which the catalyst within the reaction zone would be exposed. Accordingly then, the better approach would be to state that a minimum total quantity based generally on the phosphorus and/or vanadium content in the reaction zone be passed into the reaction zone for regeneration conditions to give the necessary selectivity increase.

Carrier gases are contemplated when the regeneration procedure occurs to move the regeneration agent through the catalyst bed. The carrier gases are not necessarily critical and can include materials such as nitrogen, butane, oxygen, or any other available gaseous stream which would be compatible with the regeneration agent and would not degrade the catalyst performance.

Regeneration and stabilization conditions include a temperature in the range generally from about 300° C. to about 550° C. In a preferred instance, the regeneration conditions suitably include a temperature within the range of from about 350° C. to about 500° C., and in some instances, from about 375° C. to about 475° C. Of course, the temperatures of regeneration will vary depending on the specific catalyst and oxidation process ultimately utilized. When normal butane and air or enriched oxygen are passed into the reaction zone for the production of maleic anhydride, it has been found that a most preferred regeneration temperature will be somewhere above 350° C., but below 500° C. when a carbon tetrachloride regeneration agent is used in conjunction with a phosphorus compound.

For the most successful regeneration and stabilization of a butane oxidation catalyst for producing maleic anhydride when using a carbon tetrachloride regeneration agent in conjunction with a phosphorus compound, it has been found that regeneration temperatures greater than about 375° C. are desired to cause increases in selectivity but less than about 475° C. are needed to reduce losses in catalyst conversion.

The halogen-containing regeneration agents which may be used in the regeneration and stabilization process disclosed herein generally include materials such as molecular halogens or mixtures thereof, or compounds containing one or more halide radicals or mixtures thereof. However, within the broad category of halides there obviously exist materials with hazardous properties, e.g., self-detonation or highly corrosive tendencies which, while within the definition of halides for regeneration agents, would not necessarily be effective since they destroy the catalyst and/or the processing equipment. Accordingly then, in defining the regeneration agents or halides used herein, the inoperative species are to be precluded.

One of the basic requirements when utilizing the halide materials as regeneration agents is that they remain in a vapor phase when employed at reactivating conditions. Accordingly then, materials which have reasonably high boiling points are not practical and would present processing difficulties. It is preferable that the halide materials be in a vapor phase at temperatures above a minimum of about 250° C. at atmospheric pressure. The specific regeneration agents can include pure components or mixtures of components. Specifically useful in the regeneration step herein are the halides including the gaseous forms of fluorine, chlorine, and bromine. In some instances, gaseous iodine may be used, but its boiling point is sufficiently high so that it may not present a favorable regeneration agent when used at low temperatures. Specific regeneration agents can include, but are not necessarily limited to the following: hydrogen chloride, trichloromethane, dichloromethane, monochloromethane, hexachloroethane, halide-substituted ethanes, propanes, butanes (normal or iso), pentanes (normal or branched), hexanes (branched or straight), and other chloride or halide-containing aliphatics. Other specific halides which can be utilized include materials such as 1,6-dichlorohexane, 1,2-dichlorohexane, 1,2-dibromohexane, 2,2-dichlorohexane, 2,3-dichlorohexane, 2,5-dichlorohexane, and 3,4-dichlorohexane, normal hexylbromide, sec-hexylbromide and 3-bromohexane.

Organic halides of fairly low carbon number (generally 4 or less) are preferred to reduce the possibility of coke formation during regeneration.

Inter halogens which may be utilized include gases which have reasonably low boiling points such as ClF, ClF$_3$, BrF, BrCl, IBr, BrF$_5$, F$_2$O, Cl$_2$O ClO$_2$ (potentially explosive), Cl$_2$O$_6$, Cl$_2$O$_7$, Br$_2$O and oxy acids of chlorine, bromine, and iodine. Other materials which may be utilizable at high reactivation temperatures include products such as CF$_4$, CHF$_3$, Freon 12, Freon 13, Freon 22, Freon 21 and trichloroacetic acid.

One class of regeneration agents includes organic halides being in the vapor state above about 250° C. at atmospheric pressure represented by the formula:

$$C(X)_n$$

where each X is a selected halide and n is an integer from 1 to 4, any remaining radicals being hydrogen. Carbon tetrachloride is representative of the group and is especially preferred.

Another class of regeneration agents include organic halides being in the vapor state above about 250° C. at atmospheric pressure represented by the formula:

$$R(X_1)_m$$

where R is alkane, alkene or alkyne of straight or branched structure having at least two carbon atoms and X$_1$ is independently a primary, secondary or tertiary halide and m is an integer of from 1 to about 20 consistent with the number of carbon atoms of said structure.

This invention also comprises a process for oxidizing butane to maleic anhydride with the regenerated and stabilized catalyst wherein in addition to the carbon halide treatment the catalyst has been treated with a phosphorus compound, particularly an alkyl ester of orthophosphoric acid, in the presence of about 1,000 to about 40,000 parts per million by weight of water based on the total weight of the feed gas stream. Generally, the amount of alkyl ester added is about 0.1 to about 100,000 parts per million by weight of the reactor feed gas stream. In a preferred mode the amount of alkyl phosphate added is in the range of about 0.1 to about 30 parts per million by weight of the reactor feed stream. Higher concentrations of alkyl phosphate generally above about 30 parts per million by weight are useful in a batch catalyst regeneration process, preferably in a range of about 50 to about 100,000 parts per million by weight of reactor feed gas stream and more preferably about 1,000 to about 100,000 parts per million by weight of reactor feed gas stream. The regeneration and stabilization is conducted at a temperature of about 300° C. to about 550° F. The alkyl phosphate in a water medium comprising about 0.001 to about 90 weight percent, more preferably about 0.01 to about 50 weight percent, of the solution is contacted with the feed gas stream flowing to the reactor. If desired, the water and alkyl phosphate may be added separately to the feed gas stream instead of as a solution. Alternatively, the alkyl phosphate and water may be added directly to the butane feed prior to the mixing of the butane and air reactants. The oxidation of butane to maleic anhydride may be accomplished by contacting n-butane in low concentration in oxygen with the described catalyst. Air is entirely satisfactory as a source of oxygen, but synthetic mixtures of oxygen and diluent gases such as nitrogen may also be employed. Air enriched with oxygen may be used.

The gaseous feed stream to the oxidation reactors will normally contain air and about 0.2 to about 1.7 mole percent of the hydrocarbon such as benzene, butane, butene or butadiene. About 0.8 to about 1.5 mole percent of the hydrocarbon is satisfactory for optimum yield of maleic anhydride for the process of this invention. Although higher concentrations may be employed, explosive hazards may be encountered. Lower concentrations of the hydrocarbon feedstock, less than about one percent, of course, will reduce the total yield obtained at equivalent flow rates and, thus, are not normally employed for economic reasons. The flow rate of the gaseous stream through the reactor may be varied within rather wide limits, but the preferred range of operations is at the rate of about 100 to about 4000 cc of feed per cc of catalyst per hour and more preferably about 1000 to about 2400 cc of feed per cc of catalyst per hour. Lower flow rates make the butane oxidation process uneconomical. A catalyst should be effective at flow rates of about 1200 to about 2400 cc of hydrocarbon feed per cc of catalyst per hour. There are catalysts which show good promise but when subjected to the hourly space velocity designated above show very poor yields. The amount of water added is about 1,000 to about 40,000 parts per million by weight of the reactor feed gas stream. The preferred amount of water added is about 5,000 to about 35,000 parts per million by weight of the reactor feed gas stream. Residence times of the gas stream will normally be less than about four seconds, more preferably less than about one second, and down to a rate where less efficient operations are obtained. The flow rates and residence times are calculated at standard conditions of 760 mm of mercury and at 0° C.

The reaction may be conducted at atmospheric, super-atmospheric, or below atmospheric pressure. The exit pressure will be at least slightly higher than the ambient pressure to ensure a positive flow from the reactor. The pressure of the inert gases must be sufficiently high to overcome the pressure drop through the reactor.

A variety of reactors will be found to be useful, and multiple tube heat exchanger-type reactors are quite satisfactory. The tops of such reactors may vary in diameter from about one-quarter inch to about three inches, and the length may be varied from about three to about ten or more feet. The oxidation reaction is an exothermic reaction and, therefore, relatively close control of the reaction temperatures should be maintained. It is desirable to have the surface of the reactors at relatively constant temperatures, and some medium to conduct heat from the reactors is necessary to aid temperature control. Such media may be Woods metal, molten sulphur, mercury, molten lead and the like, but it has been found that eutectic salt baths are completely satisfactory. One such salt bath is a sodium nitrate, sodium nitrite, potassium nitrate eutectic constant temperature mixture. An additional method of temperature control is to use a metal block reactor whereby the metal surrounding the tube acts as a temperature regulating body. As will be recognized by one skilled in the art, the heat exchanger medium is suitably kept at the proper temperature by heat exchangers and the like. The reactor or reaction tubes are suitably iron, stainless steel, carbon steel, nickel, glass tubes, such as vycor and the like. Both carbon steel and nickel tubes have excellent long life under the conditions of the reaction described herein. Normally, the reactors contain a preheat zone under an inert material such as one-quarter inch alundum pellets, inert ceramic balls, nickel balls, or chips and the like present at about one-half to one-tenth the volume of the active catalyst present.

The temperature of reaction may be varied within some limits, but normally the reaction should be conducted at a temperature within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than 20°–50° F. above the salt bath temperature. The temperature of the reactor, of course, will also depend to some extent upon the size of the reactor and the butane concentration.

Maleic anhydride may be recovered by a number of ways well-known to those skilled in the art. For example, the recovery may be by direct condensation or by absorption in suitable media, with specific operations and purification of the maleic anhydride.

In order to more adequately understand and describe the novel regeneration and stabilization process the following definition of terms is presented.

$$\text{Conversion} = \frac{\text{moles hydrocarbon feed consumed}}{\text{moles hydrocarbon charged}}$$

$$\text{Selectivity} = \frac{\text{moles desired oxidation product produced}}{\text{moles hydrocarbon feed consumed}}$$

Mole Yield = (Conversion) (Selectivity)

In a specific instance wherein a feed stream containing essentially normal butane is charged to the reaction zone for the production of maleic anhydride, the conversion, selectivity and mole yield are shown below.

$$\text{Conversion} = \frac{\text{moles n-C}_4 \text{ consumed}}{\text{moles n-C}_4 \text{ charged}}$$

$$\text{Selectivity} = \frac{\text{moles maleic anhydride produced}}{\text{moles n-C}_4 \text{ consumed}}$$

-continued

Mole Yield = (Conversion) (Selectivity)

In instances in which a weight yield is desired for the production of maleic anhydride from normal butane, the following calculation can be used.

Weight Yield = (Conversion)(Selectivity)(1.69)

The above conversion, selectivity and yields on the molar basis times 100 equal percentage conversion, selectivity and mole yields. When determining a weight yield, it is necessary to know the ratio of the molecular weights of the feed hydrocarbon and the oxygenation product and, accordingly, the weight yield for the production of maleic anhydride from normal buane is defined as the product of the molar conversion times the molar selectivity (for normal butane to maleic anhydride), all times 1.69. The theoretical maximum production of maleic anhydride from normal butane would give a weight yield of 1.69 pounds of maleic anhydride for each pound of normal butane consumed, assuming 100 percent selectivity and conversion. In stating the weight yield on a percentage basis, it merely reflects the quantity of theoretical weight yield of maleic anhydride times 100. Accordingly then, the theoretical weight percent yield would be 169 percent.

The following examples are presented to specifically illustrate certain embodiments of the claimed regeneration and stabilization process herein; and are not necessarily presented so as to unduly limit or restrict the scope of the claims:

EXAMPLES

The maleic anhydride yield of a phosphorus-vanadium-oxygen catalyst in a pilot plant having a 33 inch catalyst bed and a 0.62 inch i.d. reactor declined to 59 wt.% at a salt bath temperature of 817° F., 1.5% n-butane in air feed, and 2000 VHSV after 3832 hours on stream. At this time, the feed stream was directed through a saturator containing an aqueous solution of triethylphosphate. During the next 5797 hours on stream, the catalyst yield at 1.5% n-butane in air and 2000 VHSV was maintained at 61-69 wt.% using aqueous triethylphosphate solutions in the feed gas saturator ranging in concentration from 1 g triethylphosphate/1 of $H_2O$ to 22 g triethylphosphate/1 of $H_2O$.

The triethylphosphate addition was then discontinued and the yield declined to 59 wt.% at 816° F. and the same n-butane concentration and flow rate after 9821 hours. The feed to the reactor was then discontinued and nitrogen at about 100 VHSV was passed over the catalyst at 810° F. $CCl_4$, 13 g, was added to the nitrogen stream in 15 minutes using a syringe pump. At 9965 hours, the yield of the catalyst was 64 wt.% at 821° F., 15% n-butane, and 2000 VHSV. The feed was passed through a saturator containing an aqueous solution of triethylphosphate with a concentration of 2-6 g triethylphosphate/1 of $H_2O$. A maximum maleic anhydride yield of 69 wt.% was achieved at 10156 hours. However, the yield declined to 65 wt.% at 10493 hours.

At 10517 hours, the triethylphosphate addition was again discontinued. At 834° F., 2000 VHSV, and 1.5% n-butane in the feed, 13 g of $CCl_4$ were injected into the feed stream using a syringe pump. The maleic anhydride yield was only 53 wt.% at 10613 hours when the feed stream was again put through a saturator containing 4 g of triethylphosphate/1 of $H_2O$. The yield improved to 69 wt.% at 837° F. and the same flow conditions after 10776 hours. A maximum maleic anhydride yield of 72 wt.% was achieved after 11160 hours at 854° F. with a saturator concentration of 8 g triethylphosphate/1 of $H_2O$. This yield was sustained for a period of one week demonstrating that this improved yield was not an excursion in the data.

This example shows that the use of $CCl_4$ followed by the addition of triethylphosphate and water improves the yield of an aged catalyst over the singular use of either method. Triethylphosphate and water treatment alone gave a maximum maleic anhydride yield of 69 wt.%. Treatment with $CCl_4$ followed by the addition of triethylphosphate and water improved the yield of 72 wt.% which is a 3 wt.% increase in yield.

I claim:

1. A catalytic process for the oxidation of n-butane to maleic anhydride wherein n-butane is contacted with a catalytic amount of vanadium phosphorus oxide catalyst having an atomic ratio of phosphorus to vanadium in the range of about 0.5 to about 5 regenerated according to the following process comprising:
   (A) contacting said catalyst at a temperature in the range of from about 300° C. to about 550° C. with an effective amount of a material selected from the group consisting of:
   (1) molecular chlorine of fluorine or mixtures thereof;
   (2) carbon halides of fluorine, chlorine, bromine or iodine being in the vapor state above about 250° C. at atmospheric pressure represented by the following formula:

$$C(X)_n$$

where each X is a selected halide and n is an integer from 1 to 4, any remaining radicals being hydrogen or mixtures thereof;
   (3) organic halides of fluorine, chlorine, bromine or iodine being in the vapor state above about 250° F. at atmospheric pressure represented by the formula;

$$R(X_1)_m$$

where R is alkane, alkene or alkyne of straight or branched structure having at least two carbon atoms and $X_1$ is independently a primary, secondary or tertiary halide and m is an integer of from about 1 to about 20 consistent with the number of carbon atoms of said structure or mixtures;
   (4) hydrogen halides or mixturs thereof at regeneration conditions including a temperature in the range of from about 300° C. to about 550° C.; and
   (B) contacting the catalyst with an effective amount of an alkyl ester of other orthophosphoric acid and water.

2. The process of claim 1 wherein the catalyst is regenerated by contacting it during the oxidation with water and the phosphorus compound, wherein the amount of water added is about 1,000 parts per million to about 40,000 parts per million by weight of the reaction feedstock.

3. A catalytic process for the oxidation of n-butane to maleic anhydride wherein n-butane is contacted with a catalytic amount of vanadium-phosphorus-oxide-cometal catalyst having an atomic ratio of phosphorus to vanadium in the range of about 0.5 to about 5 comprising:
(A) contacting said catalysft at a temperature in the range of from about 300° C. to about 550° C. with an effective amount of a material selected from the group consisting of:
(1) molecular chlorine or fluorine or mixtures thereof;
(2) carbon halides of fluorine, chlorine, bromine or iodine being in the vapor state above about 250° C. at atmospheric pressure represented by the following formula:

$$C(X)_n$$

where each X is a selected halide and n is an integer from 1 to 4, any remaining radicals being hydrogen or mixtures thereof;
(3) organic halides of fluorine, chlorine, bromine or iodine being in the vapor state above about 250° C. at atomospheric pressure represented by the formula:

$$R(X_1)_m$$

where R is alkane, alkene or alkyne of straight or branched structure having at least two carbon atoms and $X_1$ is independently a primary, secondary or tertiary halide and m is an interger of from about 1 to about 20 consistent with the number of carbon atoms of said structure or mixtures;
(4) hydrogen halides or mixtures thereof at regeneration conditions including a temperature in the range of from about 300° C. to about 550° C.; and
(B) contacting the catalyst with an effective amount of an alkyl ester of orthophosphoric acid and water.

4. The process of claim 3 wherein the cometal is selected form the group of zinc and molybdenum.

5. The process of claim 4 wherein the catalyst is regenerated according to claim 2.

6. The process of claim 1 wherein the oxidation is conducted at a temperature of about 700° F. to about 900° F.

7. The process of claim 3 wherein the oxidation is conducted at a temperature of about 700° F. to about 900° F.

8. The process of claim 4 wherein the oxidation is conducted at a temperature of about 700° F. to about 900° F.

9. The process of claim 3 wherein the cometal is selected from the group of zinc, bismuth, copper, molybdenum, lithium, tungsten, chromium, uranium, niobium, zirconium, tin, cobalt, iron, nickel, antimony, titanium, or mixtures thereof.

10. The process of claim 9 wherein the oxidation is conducted at a temperature of about 700° F. to about 900° F.

* * * * *

UNITED STATES PATENT OFFICE
CERTIFICATE OF CORRECTION

Patent No. 4,918,201     Dated April 17, 1990

Inventor(s) Robert C. Edwards

It is certified that error appears in the above-identified patent and that said Letters Patent is hereby corrected as shown below:

| Col. | Line | |
|---|---|---|
| 2 | 66 | "air feed" should read --air fed-- |
| 7 | 49 | "isabout" should read --is about-- |
| 10 | 15 | "of" should read --to-- |
| 11 | 4 | "catalysft" should read --catalyst-- |
| 10 | 43 | "formula;" should read --formula:-- |

Signed and Sealed this

Seventh Day of April, 1992

Attest:

HARRY F. MANBECK, JR.

*Attesting Officer*     *Commissioner of Patents and Trademarks*